United States Patent [19]

Boettcher et al.

[11] Patent Number: 5,194,265
[45] Date of Patent: Mar. 16, 1993

[54] INSECTICIDE DEVICES

[75] Inventors: Thomas E. Boettcher; Byron D. Fair, both of St. Paul, Minn.

[73] Assignee: Minnesota Mining and Manufacturing Company, St. Paul, Minn.

[21] Appl. No.: 725,418

[22] Filed: Jul. 1, 1991

Related U.S. Application Data

[63] Continuation of Ser. No. 329,531, Mar. 28, 1989, abandoned.

[51] Int. Cl.$^5$ ............................................. A01N 25/34
[52] U.S. Cl. ....................................... 424/411; 424/486
[58] Field of Search ........................... 424/411, 81, 486

[56] References Cited

U.S. PATENT DOCUMENTS

| | | | |
|---|---|---|---|
| 3,873,725 | 3/1975 | Skinner et al. | 424/DIG. 10 |
| 3,876,762 | 4/1975 | Rabusser et al. | 424/78 |
| 3,991,213 | 11/1976 | Mitsubayashi | 514/134 |
| 4,137,279 | 1/1979 | Smith et al. | 260/861 |
| 4,189,467 | 2/1980 | von Bittera et al. | 424/14 |
| 4,195,075 | 3/1980 | Miller | 424/78 |
| 4,218,294 | 8/1980 | Brack | 525/440 |
| 4,526,920 | 7/1985 | Sakashita et al. | 524/548 |
| 4,536,388 | 8/1985 | Pearce, III | 424/411 |
| 4,543,247 | 9/1985 | von Bittera et al | 424/78 |
| 4,543,367 | 9/1985 | Rutherford et al. | 424/78 |
| 4,544,547 | 10/1985 | von Bittera | 424/78 |
| 4,548,764 | 10/1985 | Manteanu et al. | 424/76.4 |

FOREIGN PATENT DOCUMENTS

| | | |
|---|---|---|
| 904548 | 4/1986 | Belgium . |
| 2386254 | 4/1978 | France . |
| 1326825 | 8/1973 | United Kingdom . |

Primary Examiner—Howard E. Schain
Assistant Examiner—Choon Koh
Attorney, Agent, or Firm—Gary L. Griswold; Walter N. Kirn; Philip M. Goldman

[57] ABSTRACT

An article for dispensing an agent having antiectoparasitic activity comprising a radiation-cured thermoset resin matrix and said agent dispersed therein. A method for using said article is also described.

18 Claims, No Drawings

INSECTICIDE DEVICES

This is a continuation of application Ser. No. 07/329,531 filed Mar. 28, 1989, now abandoned.

TECHNICAL FIELD

This invention relates to articles for dispensing an insecticide and to a method for using the same.

BACKGROUND OF THE INVENTION

Ectoparasite control has been a goal of mankind throughout history. Devices having insecticidal activity and designed for use on animals such as livestock, companion animals and the like have been known for some years. For example, there are a number of commercially-available devices such as livestock ear tags which comprise an insecticide dispersed throughout a plasticized thermoplastic matrix. Examples of such devices are Terminator TM (available from Fermenta) and Tomahawk TM (available from Coopers). Thermoplastic devices such as the foregoing typically weigh 10 grams or more and contain substantial amounts of plasticizer.

Further, U.S. Pat. No. 4,195,075 which discloses an insecticidal livestock ear tag comprising a plasticized thermoplastic matrix also discloses that thermoset matrices such as a polyurethane are useful. In such an embodiment, the particular insecticide disclosed in said patent is said to act as an external plasticizer.

The prior art has not taught an antiectoparasite device comprising a bioactive agent incorporated in a radiation-cured thermoset resin.

BRIEF DESCRIPTION OF THE INVENTION

The present invention provides a novel article for dispensing an agent having anti-ectoparasitic activity, comprising a thermoset resin matrix curable by free radical polymerization and the agent dispersed in the resin matrix, the article being substantially flexible and the agent being present in an amount and of a type which provides for release of the agent in an anti-ectoparasitically effective amount over a prolonged period. The agent may be, for example, an insecticide, a pheromone and/or a repellent. The article may be in the form of a film, sheet, shaped article or the like. In preferred embodiments, the article takes the form of a livestock ear tag or tail tag or a pet collar or insecticidal strips. A method for using such an article is also provided by this invention.

The articles of the invention are convenient to manufacture and provide for prolonged anti-ectoparasitic activity with delivery of a substantial amount of the agent originally contained in the article. Further, the articles are flexible and lightweight which significantly facilitates their use as livestock ear tags and pet collars.

DETAILED DESCRIPTION OF PREFERRED EMBODIMENTS

As used in the instant specification and claims, the phrase "anti-ectoparasitic activity" means the killing or repelling of ectoparasites. Further, the phrase "prolonged period" means that the article provides antiectoparasitic activity for a period of at least about one month. Still further, the phrase "substantially flexible" means the article may be bent back upon itself at least a single time without breaking. Finally, the phrases "acrylated polyester", "acrylated polyurethane", "acrylated epoxies" and "acrylated caprolactone" denote polymers having the indicated polymeric component as the primary polymer backbone terminated with acrylate functional end groups.

The radiation-cured thermoset resin matrix is prepared from components which are radiation-polymerizable to form a tough, but flexible material when in film-form (e.g., when prepared in a thickness of about 10 to 50 mils).

The radiation-cured thermoset resin matrix preferably is prepared from an aliphatic or cycloaliphatic oligomer (i.e., a component having an average molecular weight generally of about 200 to 20,000) and optionally, but preferably, an aliphatic or cycloaliphatic monomer (i.e., a component having an average molecular weight of less than about 1000). The oligomer and monomer have at least one or more terminal or pendant moieties which provide for free radical polymerizability and cross-linking. Free radical polymerizable moieties which may be present include alpha, beta-unsaturated carboxylic acid groups such as acrylate or methacrylate groups. The resin matrix will contain from about 0 to 100%, preferably about 10 to 90%, and most preferably 10 to 50% by weight of the monomer based on the total weight of the polymerizable components contained in the resin matrix (i.e., excluding the weight of any non-polymerizable components such as a scrim, etc.).

Acrylated oligomers can be prepared from the reaction of a polyol with a diisocyanate in excess, and the residual isocyanate is reacted with a chain terminator. The chain terminator may have, for example, at least a hydroxyl and a vinyl functional group.

The diisocyanate employed in preparing the oligomer may be, for example, 1,4-cyclohexyl diisocyanate, 4,4-methylenebiscyclohexyl diisocyanate, hexamethylene diisocyanate, isophorone diisocyanate, 2,5-toluene diisocyanate, 2,2,4-trimethylhexamethylene diisocyanate(TMDI).

The polyol employed in preparing the oligomer may be, for example, polyethylene glycol; polypropylene glycol; polyester polyol such as Inolex TM 3500-90 or Inolex TM 1400-35 available from Inolex TM polycaprolactone polyol such as Tone TM 0200, Tone TM 0305 and Tone TM 0310 available from Union Carbide. The term polyol is defined for purposes of the present invention as any molecule containing two or more hydroxyl groups with a molecular weight greater than 50.

The chain terminator used in preparing the oligomer may be, for example, hydroxyethyl acrylate, hydroxyethyl methacrylate, hydroxypropyl acrylate or hydroxypropyl methacrylate.

Other types of oligomers which may be used in the practice of the invention are the reaction product of a diisocyanate with two equivalents of chain terminator such as the chain terminators mentioned above.

Still further examples of types of oligomers which may be employed are the acrylated epoxy resins. The epoxy oligomers may be, for example, reaction products from acrylated esters of aromatic/aliphatic epoxy, for example, the diacrylate ester of a bisphenol A-type epoxy.

The preferred oligomers employed in the practice of this invention are either the reaction product of a polycaprolactone polyol (for example, above-mentioned Tone TM 0310) reacted with above-mentioned TMDI and chain terminated with hydroxyethyl acrylate; or a urethane acrylate available under the trade designation Uvithane 893 from Morton Thiokol.

The aliphatic or cycloaliphatic monomer suitable for use in the practice of the invention may be, for example, a mono- or multifunctional acrylate or methacrylate, such as tetrahydrofuran acrylate, isobornyl acrylate, isobornyl methacrylate, beta-hydroxyethylmethacrylate, 1,6-hexanediol diacrylate, triethylene glycol diacrylate, triethylene glycol dimethacrylate, tetraethylene glycol diacrylate, tetraethylene glycol dimethacrylate, neopentyl glycol diacrylate, neopentyl glycol dimethacrylate, trimethylolpropane triacrylate(TMPTA), trimethylolpropane trimethacrylate, pentaerythritol triacrylate or pentaerythritol tetracrylate.

Also useful as the monomer is the reaction product of TMDI with hydroxyethyl acrylate or TMDI with hydroxyethyl methacrylate or TMDI with two equivalents of polypropylene glycol monomethacrylate (e.g., that available under the trade designation Sipomer® PPGMM from Alcolac). The preferred monomer is the reaction of TMDI with polyethylene glycol monomethacrylate (e.g., that available under the trade designation Sipomer® HEM 10 from Alcolac).

The anti-ectoparasitic agent will be present in the resin matrix in an amount which provides for release of the agent in an anti-ectoparasitically effective amount over a prolonged period. The anti-ectoparasitic agent will be present in the article in an amount of about 1 to 50 parts per 100 parts by weight of the polymerizable components of the resin matrix. Preferably, the agent will be present in an amount of about 1 to 30 parts by weight per 100 parts by weight of the polymerizable components of the resin matrix. The agent becomes dispersed in the uncured resin matrix and is preferably soluble in the uncured resin in the amount which is included therein.

The anti-ectoparasitic agent employed in the practice of the invention may be, for example, an insecticide, pheromone or repellent. Suitable organophosphate insecticides are trichlorfon, cyanofenphos, fonofos, dichlorvos, naled, mevinphos, phosphamidon, monocrotophos, tetrachlorvinphos, chlorfenvinphos, crotoxyphos, cruformate, fenitrothion, dicapthon, fenthion, fensulfothion, temephos, mercaptophos, malathion, phorate, diazinon, chlorpyrifos, chlorpyrifos methyl, coumaphos, azinphosmethyl, methamidophos, acephate, parathion, pirimiphos ethyl, pirimiphos methyl, phosmet, cythioate, dermaton, fospirate, dimethoate and methyl parathion. Suitable carbamate insecticides are carbaryl, aldicarb, carbofuran and propoxur. Suitable pyrethroid insecticides are pyrethrum, permethrin, resmethrin, fenvalerate, deltamethrin, esbiothrin and tetramethrin.

Suitable pheromones are muscamone, gossyplure, integralure, disparlure and grandlure.

Suitable repellents are dimethyl phthalate, dibutyl phthalate, 2-ethyl-1,3-hexanediol, benzyl benzoate, oil of rue, oil of eucalyptus, oil of cedar, oil of citronella, oil of penroyal and deet.

Other active agents include lindane, amitraz, methoprene, d-limonene and rotenone.

Plasticizer compounds, known to one skilled in the art, may be incorporated, but are not required for release or delivery of the anti-ectoparasitic agent from the articles of the invention.

The release rate of the anti-ectoparasitic agent may be tailored by appropriate selection of the oligomer, monomer and active agent and the relative amounts of each.

The release of the anti-ectoparasitic agent will vary with molecular weight and radiation polymerizable functionality of the oligomer and monomer as well as the type and percent loading of the active agent employed.

In vitro studies have shown that there is generally a direct correlation between molecular weight of the oligomer and release rate of the active, molecular weight being defined as the weight of the polyol backbone. A decrease in molecular weight of the oligomer generally results in a corresponding decrease in release rate when keeping the active agent and the monomer the same. The release rate being defined as amount of active agent released per unit time.

Oligomers with similar molecular weight but different functionality such as, for example, difunctional Tone TM 0200 (MW 524), and trifunctional Tone TM 0305 (MW 537) generally will have release rates that are different for the same active agent. Generally, increasing oligomer functionality tends to reduce the release rate of the active agent.

An increase in loading of the active agent generally will change the release rate of the active for a given resin system.

The type, molecular weight and weight percent of the monomer employed in the practice of this invention will also affect the release rate of the active agent.

The ratio of oligomer to monomer will also generally affect the release of the active agent.

In this invention, slow release of an active agent can be achieved by combining a low molecular weight multifunctional oligomer and a low molecular weight multifunctional monomer, for example, the trifunctional oligomer Tone 0305/TMDI/Hydroxyethyl acrylate diluted with TMPTA.

In this invention, the release rate of an anti-ectoparasitic agent over a prolonged period depends not only on the resin components but also on selection of the active agent. A change in active agent, for a selected resin system, can result in a different release rate.

The articles of the invention are prepared by free radical polymerization which may be accomplished using any conventional free radical method such as electron beam, visible light, thermal curing or ultraviolet light methods, the latter being most preferred. Any conventional catalyst such as a photosensitizer may be used to facilitate cure according to the method employed. Examples of suitable photosensitizers for an ultraviolet cure are Irgacure TM 651 (available from Ciba-Geigy) and Darocur TM (available from EM Industries, Inc).

The resin matrix of the article of the invention may be reinforced through employment of a material. The reinforcement material may be, for example, a cloth, scrim or polymeric film. Examples include woven, nonwoven, open weave, stitch bonded or spun bonded material or any combination thereof. Suitable reinforcement materials include TyVek® available from Dupont; TyPar® and Reemay® available from Reemay, Inc.; Stabilon® available from Milliken and Company; Celestra® available from James River; Melinex® available from ICI; stitchbonded cloth available from Milliken and Company and West Point Pepperell Company; polyester, cotton, rayon, nylon and cotton/polyester blends of cloth available from Milliken and Company and West Point Pepperell Company. Alternatively, reinforcement of the article may be accomplished, for example, by inclusion of glass fibers or staple fibers.

Other ingredients such as stabilizers, attractants, dyes, fillers, colorants, antioxidants, UV absorbers or other biocides can also be used in the articles of the invention without departing from the scope of this invention.

The articles of the invention may be used to kill ectoparasites found on and/or repel ectoparasites from an animal such as a cow (e.g., in the case of beef cattle) or a companion animal (e.g., a dog). The article is attached to the animal for a period sufficient to so kill and/or repel the ectoparasites to the desired extent.

When in the form of a flea collar, any conventional fastening means such as buckle, pressure-sensitive adhesive, staple, hook & loop, or rivets may be employed. Examples of fasteners found in U.S. Pat. Nos. 4,031,859, 4,180,016 and 3,765,376 may be employed in the practice of this invention, the disclosures of each patent being incorporated herein by reference.

When in the form of an ear tag, the fastening means may be any known to the art such as single element or band means as well as two piece fastening systems such as clamps, pins or studs. Examples of suitable fastening means are disclosed in U.S. Pat. Nos. 3,184,874, 3,260,007, 3,595,201, 3,388,492, 3,731,414 and 3,942,480, the disclosures of each of which being incorporated herein by reference.

It is believed that the articles of the invention may also find utility when employed in fruit orchards, telephone cable conduit, structures and other settings where insect control may be important.

The articles of the invention may be prepared by mixing the various ingredients including the anti-ectoparasitic agent, coating or shaping the mixture as desired, and irradiating the resulting material using the desired radiation source. Alternatively, resin can be coated on a reinforcing member prior to curing.

The examples which follow serve to further illustrate the present invention but should not be considered as limiting.

EXAMPLE 1

An article according to the invention was prepared as follows:

Part A

To a two gallon stainless steel beaker which is jacketed with an ice water bath is added 1,000 g of 2,2,4-trimethylhexamethylene diisocyanate. While stirring the contents using a mixer, 1.5 g of p-methoxyphenol and 1.0 g of dibutyl tin dilaurate were added to the beaker. Over about a forty-five to sixty minute period, 5,025 g of polyethylene glycol$_{10}$ monomethacrylate (available under the trade designation Sipomer ® HEM 10 from Alcolac) was added. The reaction exotherm was maintained at 35° C. both during the addition and for a further two hours after completion of the addition. The reaction was then heated to 65°–75° C. for three to four hours, the time depending upon residual isocyanate which was monitored by IR spectroscopy. Throughout the reaction, the reaction mixture was covered with a blanket of dry air.

Part B

Sixty-four g of Uvithane ® 893 (an acrylated urethane available from Morton Thiokol Corporation), 16 g of the monomer obtained in Part A above, 20 g of Dursban ® brand chlorpyrifos (available from The Dow Chemical Company), and 1.5 g of Irgacure ® 651 (available from Ciba Geigy) were combined in a glass jar which was then placed into a 40° C. water bath for 30 minutes after which the solution was mixed until homogeneous. The mixture was then left standing to degas.

Part C

The mixture from Part B above was coated simultaneously on both sides of a polyester cloth reinforcing scrim sandwiched between two layers of a 4 mil polyester film. The coating was done using a notch bar coater with a gap set at 15 mils. The film was used to facilitate the coating.

The wet samples from above were irradiated using a Radiation Polymer Corp. QC-126244ANIR processor having two medium pressure mercury vapor lamps set at 200 watts per inch in a nitrogen environment. The line speed was 30 feet per minute.

EXAMPLES 2–4

Further embodiments of the invention were prepared generally according to the procedures of Example 1 except that the amount of the monomer from Part A was 24 g and the weight of Uvithane ® 893 was 56 g and the type and amount of the anti-ectoparastic agent were as follows:

| Example | Anti-Ectoparasitic Agent |
| --- | --- |
| 2 | 20 g Dursban ® (chlorpyrifos, available from The Dow Chemical Company) |
| 3 | 20 g Sendran ® (propoxur, available from Mobay) |
| 4 | 20 g Rabon ® (tetrachlorvinphos, available from Fermenta) |

EXAMPLE 5

The articles according to Examples 1–4 were slit into flea collars having a dimension of ⅜-inch × 24 inches. The collars were fitted to the necks of the dogs and fastened using staples. Excess collar was trimmed off. Twelve dogs were divided into four groups with each group having uniformity in difference in size, color and hair length. Approximately one-half of the dogs in each group were females and half were males. The dogs were preconditioned and weighed at the beginning of the trial. The dogs were housed 1 to 2 dogs per cage and were group isolated. Four days before Day 0 and on each of Days 6 and 13, each dog was infested with one hundred unfed, adult fleas which were placed along the dorsal midline of each dog from its head to the base of its tail. Fleas on each dog were counted on Days 0, 1, 3, 7 and 14. To each group was applied a different one of the collars obtained from Examples 1–4 on Day 0. Results were as indicated in the table below:

Day 0 is the day the collar is put on. Day 1 is the next day.

| Flea Collar from Example | Number of Fleas | | | | |
| --- | --- | --- | --- | --- | --- |
| | Day 0 | Day 1 | Day 3 | Day 7 | Day 14 |
| 1 | 147 | 58 | 3 | 2 | 0 |
| 2 | 133 | 94 | 12 | 2 | 5 |
| 3 | 151 | 23 | 1 | 0 | 0 |
| 4 | 147 | 107 | 56 | 39 | 24 |

As indicated above the flea collars of the invention resulted in significant flea control over a fourteen-day period.

EXAMPLE 6

A further article according to the invention was prepared as follows:

Part A

In a two gallon stainless steel beaker were combined 1886 g of 2,2,4-trimethylhexamethylene diisocyanate, 1.5 g of dibutyl tin dilaurate and 2 g of methylethyl hydroquinone. Surrounding the beaker was an ice bath supported by a hot plate. The beaker was continuously purged with a blanket of dried air during the reaction. Hydroxyethyl acrylate, 1060 g, was added slowly over a 30 minute period while maintaining the exotherm temperature at 40° C. or less. Thirty minutes after the addition of the hydroxyethyl acrylate, 3000 g of Tone TM 0310 (a caprolactone polyol commercially available from Union Carbide) was added slowly to the mixture over 45 to 60 minutes. The exotherm temperature was maintained below 50° C. The water bath was heated slowly until the mixture was 80° to 85° C. and the temperature was maintained for four to six hours depending upon residual isocyanate content which should be less than about 1% when analyzed by infrared spectroscopy.

Part B 64 g of the oligomer obtained in Part A above, 16 g of the monomer obtained in Example 1, Part A, 20 g of permethrin and 1.5 g of Irgacure ® 651 were combined according to the procedures of Example 1, Part B.

Part C

Scrim-reinforced samples were prepared according to the procedures of Example 1, Part C.

EXAMPLES 7-9

Further embodiments of invention were prepared generally according to procedures of Example 6 except that the type and amount by weight of the anti-ectoparastic agent were as follows:

| Example | Anti-ectoparasitic agent |
|---------|--------------------------|
| 7 | 20 g pyrethrum |
| 8 | 10 g/10 g Dursban ®/pyrethrum |
| 9 | 20 g Dusban ® |

The pyrethrum used in Examples 7 and 8 was synergised with piperonyl butoxide (PBO) and MGK-264 ® (both available from McLaughlin Gormley King) in the ratio 1:2:3.3 pyrethum:PBO:MGK-264.

EXAMPLE 10

The articles according to Examples 6-9 were slit into flea & tick collars having a dimension of ⅜-inch by 24 inches. 20 dogs divided into five groups with each group having uniformity in difference in size, sex and hair-coat length. The dogs were preconditioned and weighed at the beginning of the trial. The dogs were housed one to two dogs per cage and were group isolated. Four days before Day 0, one hundred fleas and fifty brown dog ticks were placed along the dorsal midline of each dog from head to the base of its tail. The dogs were reinfested with 100 fleas on Days 6, 13, 20 and 27 and reinfestated with 50 ticks on Days 4, 11, 18 and 25. Fleas on each dog were counted on Day 0, before attachment of collars, as well as on Days 1, 2, 3, 7, 14, 21 and 28. Tick counting for each dog was done on Days 0, 2, 3, 7, 14, 21 and 28. The different collars obtained from Example 6-9 were applied to four of the groups. The final group was a negative control. The collars were fitted to the diameter of the neck, fastened with a staple and the excess collar trimmed away. Results were as indicated in the tables below:

TABLE

Clinical Collar Evaluation: Total Flea Counts vs. Time

| Day | Control | Ex. 6 | Ex. 7 | Ex. 8 | Ex. 9 |
|-----|---------|-------|-------|-------|-------|
| 0 | 248 | 159 | 202 | 184 | 208 |
| 1 | 256 | 172 | 217 | 142 | 96 |
| 2 | 230 | 149 | 207 | 68 | 34 |
| 3 | 215 | 149 | 207 | 68 | 12 |
| 7 | 305 | 126 | 352 | 67 | 9 |
| 14 | 335 | 117 | * | 45 | 0 |
| 21 | 350 | 164 | * | 39 | 0 |
| 28 | 306 | 180 | * | 10 | 0 |

*Trial terminated after 7 days

TABLE

Clinical Collar Evaluation: Total Tick Counts vs Time

| Day | Control | Ex. 6 | Ex. 7 | Ex. 8 | Ex. 9 |
|-----|---------|-------|-------|-------|-------|
| 0 | 86 | 59 | 65 | 62 | 60 |
| 2 | 78 | 27 | 55 | 43 | 30 |
| 3 | 67 | 14 | 35 | 14 | 24 |
| 7 | 109 | 9 | 76 | 45 | 17 |
| 14 | 101 | 10 | * | 29 | 6 |
| 21 | 123 | 9 | * | 17 | 12 |
| 28 | 102 | 14 | * | 34 | 0 |

*Trial terminated after 7 days

EXAMPLE 11

55 g of the oligomer obtained in Example 6, Part A, 14 g of the monomer obtained in Example 1, Part A, 30 g of permethrin and 1.5 g of Irgacure 651 were combined according to the procedures of Example 1, Part B.

Part B

Scrim-reinforced samples were prepared according to the procedures of Example 1, Part C.

Part C

The above article was transformed by die cutting into triangular ear tags.

EXAMPLE 12

A further ear tag of this invention was prepared according to the procedures of Example 11 except that the amounts of the oligomer from Example 6, Part A, and the monomer from Example 1, Part A were 60 g and 15 g, respectively, and 25 g of diazinon was employed instead of permethrin.

EXAMPLE 13

The ear tags of Examples 11 and 12 were tested on beef cattle as follows with one ear tag being attached to each ear of each beef cow using a conventional attachment method.

Two different cattle herds with similar horn fly burdens were used for the trial. The herds consisted of animals of the same size and of similar age, breed, and sex. Test groups did not share a common fence line or loafing area. All pastures were of similar terrain.

Fly counts were made with the use of binoculars. Counts were reported as the number of flies per animal at each counting period. Percent reduction was calculated by comparing the fly counts on the tagged animals with those of the control herd. Fly counts were made prior to tagging (i.e., Day 0), Days 7, 14 and then approximately every seven days, until the trial was terminated. Fly counts were made on a minimum of 10 animals in each herd for each counting period.

The cattle were observed before and after tagging for physical condition and for any adverse reactions.

Results were as follows in the table below.

| Day | Control Count | Ex. 11 Count | Ex. 11 % Reduction | Ex. 12 Count | Ex. 12 % Reduction |
|---|---|---|---|---|---|
| 0 | 1075 | 1150 | 0.00 | 1250 | 0.00 |
| 7 | 825 | 2 | 99.76 | 55 | 93.33 |
| 14 | 900 | 0 | 100.00 | 0 | 100.00 |
| 20 | 850 | 0 | 100.00 | 12 | 98.59 |
| 27 | 875 | 18 | 97.94 | 187 | 78.63 |
| 34 | 850 | 5 | 99.41 | 200 | 76.47 |
| 41 | 800 | 15 | 98.13 | 275 | 65.63 |
| 49 | 625 | 3 | 99.52 | 400 | 36.00 |
| 56 | 800 | 5 | 99.38 | 1000 | 0.00 |
| 62 | 650 | 7 | 98.92 | * | * |
| 69 | 825 | 8 | 98.55 | * | * |
| 77 | 700 | 12 | 98.29 | * | * |
| 83 | 650 | 20 | 96.92 | * | * |
| 90 | 725 | 15 | 97.93 | * | * |
| 99 | 800 | 35 | 95.63 | * | * |
| 105 | 850 | 100 | 88.24 | * | * |
| 112 | 800 | 150 | 81.25 | * | * |
| 119 | 850 | 200 | 76.47 | * | * |
| 126 | 850 | 250 | 70.59 | * | * |
| 134 | 800 | 275 | 65.63 | * | * |
| 139 | 1000 | 350 | 65.00 | * | * |
| 147 | 1000 | 400 | 60.00 | * | * |

*Trial was terminated after 8 weeks

As can be seen from the above table, the ear tags of Examples 11 and 12 of the invention provided varying duration of fly control as a result of the differences in the composition of the two ear tags.

What is claimed is:

1. An article for dispensing an agent having anti-ectoparasitic activity comprising
  (1) a thermoset resin matrix comprising one or more aliphatic or cycloaliphatic monomers or one or more oligomers, or both, said monomers and oligomers having at least one terminal or pendant acrylate or methacrylate moiety cured by free radical polymerization, and
  (2) said agent dispersed in said resin matrix, said article being substantially flexible and said agent being present in an amount and of a type which provides for release of said agent in an anti-ectoparasitically effective amount over a prolonged period.

2. An article according to claim 1, wherein said resin matrix comprises oligomer selected from the group consisting of an acrylated polyester, an acrylated urethane, and acrylated caprolactone and acrylated epoxy.

3. An article according to claim 1, wherein said resin matrix comprises monomer selected from the group consisting of an isobornyl acrylate, 1,6-hexanediol diacrylate, trimethylolpropane triacrylate, the reaction product of 2,2,4-trimethylhexamethylene diisocyanate with two equivalents of propylene glycol monomethacrylate, and the reaction product of 2,2,4-trimethylhexamethylene diisocyanate with two equivalents of polyethylene glycol monomethacrylate.

4. An article according to claim 1, wherein said agent is selected from the group consisting of an insecticide, a pheromone, and a repellent.

5. An article according to claim 4, wherein said agent is an insecticide.

6. An article according to claim 5, wherein said insecticide is selected from the group consisting of chlorpyrifos, propoxur, tetrachlorvinphos, pyrethrum and permethrin.

7. An article according to claim 1, wherein said antiectoparasitic agent is present in an amount of about 3 to 30 parts per 100 parts of the polymerizable components of said resin matrix.

8. An article according to claim 1, wherein said resin matrix is reinforced by a fabric scrim.

9. An article according to claim 1, in the form of an ear tag.

10. An article according to claim 1, in the form of a collar.

11. An article according to claim 1, in the form of a tail tag.

12. An article according to claim 1, in the form of a strip.

13. An article according to claim 1, wherein said resin matrix is cured by thermal polymerization.

14. An article according to claim 1, wherein said resin matrix is cured by ionizing radiation.

15. An article according to claim 1 wherein said resin matrix is ultraviolet radiation-cured.

16. A method for using an article according to claim 1 to kill ectoparasites found on or repel ectoparasites from an animal, said method comprising attaching said article to said animal and allowing said article to remain so attached for a period sufficient to so kill or repel said ectoparasites.

17. A method according to claim 16, wherein said animal is a cow and said article is in the form of an ear tag.

18. A method according to claim 16, wherein said animal is a companion animal.

* * * * *

UNITED STATES PATENT AND TRADEMARK OFFICE
CERTIFICATE OF CORRECTION

PATENT NO. : 5,194,265
DATED : March 16, 1993
INVENTOR(S) : Thomas E. Boettcher, Byron D. Fair It is certified that error appears in the above-indentified patent and that said Letters Patent is hereby corrected as shown below:

Col. 7, line 52      "MGK-264®" should read --MGK-264™--

Signed and Sealed this

Thirteenth Day of June, 1995

Attest:

BRUCE LEHMAN

*Attesting Officer*      *Commissioner of Patents and Trademarks*